(12) United States Patent
Kokubo et al.

(10) Patent No.: US 6,258,799 B1
(45) Date of Patent: Jul. 10, 2001

(54) AQUEOUS COATING COMPOSITION AND PROCESS FOR PREPARING SOLID PHARMACEUTICAL PREPARATION

(75) Inventors: Hiroyasu Kokubo; Yuichi Nishiyama, both of Nakakubiki-gun (JP)

(73) Assignee: Shin-Etsu Chemical Co. Ltd., Tokyo (JP)

( * ) Notice: Subject to any disclaimer, the term of this patent is extended or adjusted under 35 U.S.C. 154(b) by 0 days.

(21) Appl. No.: 09/404,754

(22) Filed: Sep. 24, 1999

(30) Foreign Application Priority Data

Sep. 25, 1998 (JP) .................................................. 10-288829

(51) Int. Cl.⁷ ............................... A61K 31/70; C08B 3/00
(52) U.S. Cl. ............................... 514/57; 536/56; 536/58; 536/63; 536/115; 536/119; 536/124
(58) Field of Search .................................. 536/63, 56, 58, 536/115, 119, 124; 514/57

(56) References Cited

U.S. PATENT DOCUMENTS

| | | | |
|---|---|---|---|
| 3,957,523 | * 5/1976 | Ohno et al. ........................... | 106/189 |
| 4,385,078 | 5/1983 | Onda et al. ........................... | 427/3 |
| 5,700,929 | 12/1997 | Kokubo et al. ........................ | 536/63 |
| 5,776,501 | 7/1998 | Kokubo et al. ........................ | 424/494 |
| 5,800,836 | * 9/1998 | Morella et al. ........................ | 424/489 |

FOREIGN PATENT DOCUMENTS

| | | |
|---|---|---|
| 195 41 333 | 5/1996 | (DE) . |
| 0 035 780 | 9/1981 | (EP) . |
| 59-167521 | 9/1984 | (JP) . |
| 59-190925 | 10/1984 | (JP) . |

OTHER PUBLICATIONS

English Abstract for JP–A 59–167521 Sept. 21, 1984.
English Abstract for JP–A 59–190925 Oct. 29, 1984.

* cited by examiner

Primary Examiner—Elli Peselev
(74) Attorney, Agent, or Firm—Millen White Zelano & Branigan

(57) ABSTRACT

An aqueous coating composition comprising hydroxypropyl methyl cellulose trimellitate typically having a mean particle size of up to 10 μm and a plasticizer is applied to a solid pharmaceutical preparation to form a coating film having acid resistance and solubility at about pH 4. The coated preparation has an improved bioavailability.

8 Claims, No Drawings

AQUEOUS COATING COMPOSITION AND PROCESS FOR PREPARING SOLID PHARMACEUTICAL PREPARATION

This invention relates to an aqueous coating composition suitable for use in forming an acid-resistant protective coating on a solid pharmaceutical preparation and a process for preparing a coated solid pharmaceutical preparation using the same.

BACKGROUND OF THE INVENTION

Enteric coatings are widely used for various purposes including the protection of acid-labile medicaments from gastric acid and the protection of gastric mucosa from irritative or attacking medicaments. Known enteric coating compositions include cellulose compounds such as cellulose acetate phthalate, cellulose acetate trimellitate, hydroxypropyl methyl cellulose phthalate, hydroxypropyl methyl cellulose acetate succinate, and carboxymethyl ethyl cellulose; vinyl compounds such as polyvinyl alcohol acetate phthalate; and acrylic compounds such as methacrylic acid-ethyl acrylate copolymers. These bases are used in coating after the polymers are dissolved in organic solvents or aqueous latexes or water dispersions of the polymers are formed.

However, since these commercially available enteric polymers have a dissolution pH in the range of 5 to 7, they suffer from a decline of bioavailability. More particularly, when the polymer is applied to a medicament whose absorption site is limited to the upper portion of the small intestine, the enteric preparation (in the form of polymer-coated tablets or granules) will travel past the absorption site before it is sufficiently dissolved to release the medicament.

As a solution to this problem, JP-A 8-133989 and 8-301790 propose hydroxypropyl methyl cellulose acetate maleate and hydroxypropyl methyl cellulose trimellitate having a dissolution pH reduced to about 4, respectively. Because of the low dissolution pH, these polymers, apart from the concept of prior art enteric coating, are expected to find an application as an acid-resistant protective coating composition specialized for protecting medicaments from strong acidity. These polymers, however, are used as solutions in organic solvents which have the danger of explosion and fire, are hazardous to the safety and hygiene of workers, and cause environmental pollution as a result of release to the atmosphere. There is also a possibility that a minor amount of solvent be left in the coated solid preparation.

SUMMARY OF THE INVENTION

An object of the invention is to provide an aqueous coating composition which enables the use in an aqueous form of hydroxypropyl methyl cellulose trimellitate which is a low pH dissolution type base. Another object of the invention is to provide a process for preparing a coated solid pharmaceutical preparation using the same.

The inventors have found that an aqueous coating composition obtained by dispersing powder particulate hydroxypropyl methyl cellulose trimellitate (sometimes referred to as HPMCT), especially having a mean particle size of up to 10 $\mu$m, in water in the presence of a plasticizer is effective in forming an acid resistant protective coating on a solid pharmaceutical preparation by spraying and drying the composition thereon. The thus coated solid preparation has an increased bioavailability.

With respect to aqueous enteric coating compositions, JP-B 56-12614 discloses a method of forming a coating composition by dispersing enteric cellulose derivative powder having a mean particle size of up to 100 $\mu$m in water containing a compatible gelling agent having a boiling point of at least 100° C.; and JP-B 58-55125 discloses the use of triethyl citrate as the gelling agent in this method. Additionally, JP-A 59-167521 and 59-190925 disclose a method of forming a coating composition by dispersing enteric cellulose derivative powder having a mean particle size of up to 10 $\mu$m in triethyl citrate-containing water.

However, the cellulose derivatives used in the prior art enteric coating compositions have a monobasic carboxylic acid introduced into a cellulose skeleton by way of ester or ether bonds, whereas HPMCT has a dibasic carboxylic acid introduced into a cellulose skeleton. Thus the prior art cellulose derivatives and the HPMCT differ in affinity to plasticizers, etc. It is the inventors' discovery that an aqueous coating composition obtained by blending the HPMCT (different from the cellulose derivatives used in the prior art enteric coating compositions) with a plasticizer exhibits good disintegration at pH 4.0 to 4.5 as demonstrated later in Examples and allows the HPMCT to exert its effect to a full extent.

In a first aspect, the invention provides an aqueous coating composition comprising hydroxypropyl methyl cellulose trimellitate and a plasticizer. Preferably the HPMCT has a mean particle size of up to 10 $\mu$m. The aqueous coating composition is suitable for use in coating on a solid pharmaceutical preparation.

In a second aspect, the invention provides a process for preparing a coated solid pharmaceutical preparation comprising the steps of spraying the aqueous coating composition to a solid pharmaceutical preparation and drying the composition to form a coating of HPMCT on the surface of the solid pharmaceutical preparation.

DESCRIPTION OF THE PREFERRED EMBODIMENTS

The hydroxypropyl methyl cellulose trimellitate (HPMCT) used herein can be synthesized by any well-known process as disclosed in JP-A 8-301790. After synthesis, the HPMCT may be ground by any well-known method, for example, in an air blast pulverizer, ball mill or vibrating mill. The HPMCT should preferably have a mean particle size of up to 10 $\mu$m, and more preferably up to 7 $\mu$m. If the mean particle size exceeds 10 $\mu$m, sometimes a large amount of the coating solution must be applied in order to form an acid resistant coating. The lower limit of the mean particle size is not critical although a particle size of 2 $\mu$m or more is recommended for practical use. With a particle size of less than 2 $\mu$m, it sometimes becomes difficult to disperse the HPMCT to primary particles by ordinary agitation, failing to achieve the desired effect.

The aqueous coating composition of the invention has the HPMCT dispersed in water in the presence of a plasticizer. The aqueous coating composition or dispersion preferably contains about 3 to 15%, more preferably about 5 to 10% by weight of the HPMCT. A low HPMCT concentration of less than 3% by weight would take a long time in coating. A high HPMCT concentration in excess of 15% by weight would be inconvenient to apply because, for example, clogging of a spray gun can occur due to the agglomeration of HPMCT particles in the dispersion.

Examples of the plasticizer used herein include triethyl citrate, glycerol triacetate (or triacetin), acetylated monoglyceride, and phthalic esters such as dimethyl phthalate, diethyl phthalate, and dibutyl phthalate.

An appropriate amount of the plasticizer added is about 20 to 60%, more preferably about 25 to 50% by weight based on the HPMCT. Amounts of less than 20% by weight correspond to the shortage of the plasticizer so that film formation might not fully take place, failing to produce a fully acid resistant coated preparation. Amounts of more than 60% by weight correspond to the excess of the plasticizer, sometimes giving rise to the problem that granules or tablets stick together during coating or storage.

The aqueous coating composition may be obtained by dispersing finely divided HPMCT in an aqueous solution containing a plasticizer such as triethyl citrate under ordinary agitation. The solution should preferably be at a temperature of 40° C. or lower in order to prevent the HPMCT from agglomerating. Most often, dispersion is carried out at room temperature.

If desired, the plasticizer may be added after the HPMCT has been dispersed.

When the coating composition is prepared, additives that can be used in drugs, for example, surfactants and protective colloids may be added in order to improve the stability of the coating composition or water dispersion. Similarly, talc, titanium oxide and silicon dioxide may be added for the purpose of preventing the pharmaceutical preparation (in the form of granules or tablets) from sticking during coating or storage. Other additives such as pigments, dyes, flavors and perfumes may also be added, if desired. A water-soluble film coating agent or acrylic aqueous latex may be added for the purpose of controlling or altering the solubility and moisture permeability of a coating film.

The solid pharmaceutical preparation to be coated with the coating composition according to the invention includes tablets, granules, fine powders and capsules. Any desired one of well-known methods may be used in coating the solid pharmaceutical preparation with the coating composition. For example, use may be made of a pan coating apparatus, pneumatic drum coating apparatus, fluidized bed coating apparatus, agitating fluidized bed coating apparatus, or tumbler coating apparatus. The coating composition is sprayed over the solid pharmaceutical preparation in such an apparatus through a spray gun, followed by drying. The spray gun used herein may have built therein a commonly used twin-fluid atomizing nozzle.

The amount of the film coated on the surface of the solid pharmaceutical preparation by such coating operation is generally about 3 to about 40% by weight based on the weight of the solid pharmaceutical preparation although the coating amount (or coverage) varies with the type, shape, size, and surface state of the solid pharmaceutical preparation and the characteristics of drug and additives in the solid pharmaceutical preparation. Before the coating composition is applied, a film coating agent such as hydroxypropyl methyl cellulose (HPMC) may be previously applied to the solid pharmaceutical preparation to form a protective film thereon for the purpose of protecting the solid pharmaceutical preparation from water that can contact the surface of the solid pharmaceutical preparation in the coating process. After the coating composition is applied, wax or a film coating agent as above may be overcoated for the purpose of improving the stability or compression resistance of the coated pharmaceutical preparation.

EXAMPLE

Examples of the invention are given below by way of illustration and not by way of limitation. All parts and % are by weight.

Example 1

(1) Preparation of Tablets

A mixture of 70 parts of lactose, 26 parts of cornstarch, and 4 parts of polyvinyl pyrrolidone (PVP K-30 by BASF) was granulated with the aid of water and dried. to this tablet-forming powder was added 0.5 part of magnesium stearate, followed by thorough mixing. Using a rotary tablet machine, the powder was compressed into tablets having a diameter of 8 mm and a weight of 200 mg. The tablets had a hardness of about 10 kg and a disintegration time of about 5 minutes.

(2) Preparation of Coating Solution

With stirring, 28.8 g of triethyl citrate was dissolved in 1246.6 g of purified water at room temperature. With stirring, 96 g of finely divided hydroxypropyl methyl cellulose trimellitate (HPMCT) was dispersed in the solution, yielding a water dispersion of HPMCT for coating. It is noted that 28.8 g of triethyl citrate corresponded to 30% of the weight of HPMCT and that HPMCT was finely divided using an air blast pulverizer model IDS-2 (Nippon Pneumatic Industry K.K.).

The HPMCT had the following degree of substitution and mean particle size.

| | |
|---|---|
| methoxyl | DS 1.44 (14.9%) |
| hydroxypropoxyl | MS 0.18 (4.6%) |
| trimellitate | DS 0.56 (35.9%) |
| mean particle size | ~4.5 $\mu$m |

Note that DS represents a degree of substitution, MS represents a molar substitution, and the mean particle size is as measured by dry laser light diffractometry (Helos & Rodos by Nippon Bunko K.K.).

A film dimensioned 1 cm×1 cm×100 $\mu$m thick was formed from HPMCT in an organic solvent. The dissolution pH of this film in McIlvaine buffer solution was measured according to a disintegration test as prescribed in the 13th revision of the Japanese Pharmacopoeia, by filling auxiliary cylinders with the film, and feeding buffer solutions having slightly different pH. The pH at which the film was dissolved in about 30 minutes was 3.9.

(3) Coating Operation

A coating apparatus with a pneumatic drum having a diameter of 30 cm (by Shin-Etsu Chemical Co., Ltd.) was charged with 1.2 kg of the tablets obtained in (1), which was coated with the water dispersion obtained in (2) under the following conditions.

Coating Conditions

Spray gun: one twin-fluid atomizing nozzle

Spray pressure: 200 kPa

Drying air temperature: 80° C.

Spraying speed: 12 g/min

Coating amount: 8% of HPMCT

Spraying was continued until the coating amount reached 8% based on the tablet weight of HPMCT. During the coating process, samples were taken out when the coating amount was 5%, 6% and 7% of HPMCT. The thus coated tablets (including the finally coated tablets and intermediately sampled tablets) were dried at 60° C. for one hour before they were subject to the following tests.

(4) Examination of Coated Tablets

Acid Resistance Test

According to a disintegration test procedure as prescribed in the 13th revision of the Japanese Pharmacopoeia, the disintegration test using No. 1 and No. 2 solutions were carried out each on six coated tablets. The results are shown in Table 1.

Disintegration at Different pH

Like the acid resistance test, the disintegration time was measured on six finally coated tablets (8% HPMCT coverage) using McIlvaine buffer solutions having different pH values instead of No. 2 solution. An average disintegration time is shown in Table 1.

Example 2

The procedure of Example 1 was repeated except that HPMCT having a mean particle size of about 8.5 $\mu$m was used. The test results of the coated tablets are shown in Table 1.

Example 3

The procedure of Example 1 was repeated except that a water dispersion for coating was obtained by dissolving 38.4 g (40% based on HPMCT) of triethyl citrate in 1237.0 g of purified water at room temperature under agitation and dispersing 96 g of finely divided HPMCT therein under agitation. The test results of the coated tablets are shown in Table 1.

Example 4

The procedure of Example 1 was repeated except that a water dispersion for coating was obtained by dissolving 24.0 g (25% based on HPMCT) of triethyl citrate in 1251.4 g of purified water at room temperature under agitation and dispersing 96 g of finely divided HPMCT therein under agitation. The test results of the coated tablets are shown in Table 1.

Example 5

The procedure of Example 1 was repeated except that a water dispersion for coating was obtained by dissolving 48.0 g (50% based on HPMCT) of triethyl citrate in 1227.4 g of purified water at room temperature under agitation and dispersing 96 g of finely divided HPMCT therein under agitation. The test results of the coated tablets are shown in Table 1.

TABLE 1

|  |  | Disintegration time (min) | | | | |
| --- | --- | --- | --- | --- | --- | --- |
|  |  | E1 | E2 | E3 | E4 | E5 |
| Acid resistance test | No. 1 solution, HPMCT coverage 5% | unchanged | 1 tablet failed | unchanged | 2 tablets failed | unchanged |
|  | No. 1 solution, HPMCT coverage 6% | unchanged | unchanged | unchanged | unchanged | unchanged |
|  | No. 1 solution, HPMCT coverage 7% | unchanged | unchanged | unchanged | unchanged | unchanged |
|  | No. 1 solution, HPMCT coverage 8% | unchanged | unchanged | unchanged | unchanged | unchanged |
|  | No. 2 solution, HPMCT coverage 8% | 8 | 7 | 9 | 8 | 8 |
| Disintegration at different pH | pH 3.5 | >120 | >120 | >120 | >120 | >120 |
|  | pH 4.0 | 14 | 13 | 16 | 13 | 15 |
|  | pH 4.5 | 9 | 8 | 10 | 8 | 10 |

The invention enables aqueous coating of HPMCT which is a low pH dissolution type base, without sacrificing the advantages characteristic of HPMCT including acid resistance and dissolution at about pH 4. A coating film having an improved bioavailability can be formed on a solid pharmaceutical preparation.

Japanese Patent Application No. 10-288829 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. An aqueous coating composition in the form of a dispersion consisting essentially of hydroxypropylmethyl cellulose trimellitate having a mean particle size of up to 10 μm dispersed in water and a plasticizer selected from the group consisting of triethyl citrate, glycerol triacetate, acetylated monoglyceride and phthalic esters, wherein said dispersion contains about 3 to 15% by weight of hydroxypropylmethyl cellulose trimellitate and wherein the amount of said plasticizer is 30 to 50% by weight based on hydroxypropylmethyl cellulose trimellitate.

2. A process for preparing a coated solid pharmaceutical preparation comprising:

spraying an aqueous coating composition onto a solid pharmaceutical preparation and drying the composition to form a coating of hydroxypropylmethyl cellulose trimellitate on the surface of the solid pharmaceutical preparation, said aqueous coating composition in the form of a dispersion consisting essentially of hydroxypropylmethyl cellulose trimellitate having a mean particle size of up to 10 μm dispersed in water and a plasticizer selected from the group consisting of triethyl citrate, glycerol triacetate, acetylated monoglyceride and phthalic esters, said dispersion containing about 3 to 15% by weight of hydroxypropylmethyl cellulose trimellitate and the amount of said plasticizer being 30 to 50% by weight based on hydroxypropylmethyl cellulose trimellitate.

3. A solid pharmaceutical composition which comprises a coating prepared from an aqueous coating composition of claim 1.

4. An aqueous coating composition of claim 1, wherein the hydroxypropylmethylcellulose trimellitate has a mean particle size of 2 to 7 μm.

5. An aqueous coating composition of claim 1, wherein the hydroxypropylmethylcellulose trimellitate is contained in the dispersion in an amount of 5 to 10% by weight.

6. A solid pharmaceutical composition according to claim 3, wherein the amount of the coating on the solid pharmaceutical composition is 3 to 40% by weight based on the total weight of the composition.

7. An aqueous coating composition of claim 1, which is free from an organic solvent.

8. The process of claim 2, wherein the aqueous coating composition is free from an organic solvent.

* * * * *